United States Patent [19]
Cotteret et al.

[11] Patent Number: 5,928,385
[45] Date of Patent: Jul. 27, 1999

[54] COMPOSITION FOR THE OXIDATION DYEING OF KERATIN FIBERS COMPRISING A COMBINATION OF AT LEAST TWO SPECIFIC PARA-PHENYLENEDIAMINE DERIVATIVES AND PROCESSES FOR DYEING KERATIN FIBERS

[75] Inventors: Jean Cotteret, Verneuil sur Seine; Marie-Pascale Audousset, Asnieres, both of France

[73] Assignee: L'Oreal, France

[21] Appl. No.: 08/877,206

[22] Filed: Jun. 17, 1997

Related U.S. Application Data

[63] Continuation of application No. 08/539,722, Oct. 5, 1995, abandoned.

[30] Foreign Application Priority Data

Oct. 7, 1994 [FR] France .................................. 94 12003

[51] Int. Cl.$^6$ ...................................................... A61K 7/13
[52] U.S. Cl. .......................... 8/410; 8/407; 8/408; 8/412; 8/416
[58] Field of Search ............................... 8/406, 407, 408, 8/410, 412, 416

[56] References Cited

U.S. PATENT DOCUMENTS

| | | | |
|---|---|---|---|
| 3,970,423 | 7/1976 | Brody et al. | 8/410 |
| 4,152,112 | 5/1979 | Bugaut et al. | 8/410 |
| 4,277,244 | 7/1981 | Bugaut et al. | 8/410 |
| 4,311,478 | 1/1982 | Bugaut et al. | 8/407 |
| 4,361,421 | 11/1982 | Bugaut et al. | 8/410 |
| 4,840,639 | 6/1989 | Husemeyer et al. | 8/410 |
| 5,500,022 | 3/1996 | Cotteret | 8/410 |

FOREIGN PATENT DOCUMENTS

| | | | |
|---|---|---|---|
| 459 901 | 12/1991 | European Pat. Off. | |
| 2156627 | 1/1973 | France . | |
| 2364888 | 9/1976 | France . | |
| 2054665 | 2/1981 | United Kingdom | 8/410 |

*Primary Examiner*—Caroline D. Liott
*Attorney, Agent, or Firm*—Finnegan, Henderson, Farabow, Garrett & Dunner, L.L.P.

[57] ABSTRACT

An oxidation dye composition for keratin fibers comprising, in a medium which is suitable for dyeing, a combination of at least two para-phenylenediamine oxidation dye precursors or the addition salts thereof with an acid, and one or more couplers, and the use thereof for dyeing keratin fibers.

19 Claims, No Drawings

COMPOSITION FOR THE OXIDATION DYEING OF KERATIN FIBERS COMPRISING A COMBINATION OF AT LEAST TWO SPECIFIC PARA-PHENYLENEDIAMINE DERIVATIVES AND PROCESSES FOR DYEING KERATIN FIBERS

This is a continuation of application Ser. No. 08/539,722, filed Oct. 5, 1995, now abandoned.

The present invention relates to a composition for the oxidation dyeing of keratin fibers and in particular of human keratin fibers, comprising a combination of at least two specific para-phenylenediamine oxidation dye precursors and, where appropriate, one or more coupling agents.

The invention also relates to the use of such a composition in the abovementioned cosmetic application.

It is known to dye keratin fibers, and in particular human hair, with dye compositions containing oxidation dye precursors, in particular ortho- or para-phenylenediamines, ortho- or para-aminophenols, generally referred to as "oxidation bases", and couplers also referred to as colour modifiers, more particularly meta-phenylenediamines, meta-aminophenols and meta-diphenols, which make it possible to modify and to enrich with glints the "foundation" colourations obtained by the condensation products of the oxidation bases.

In the field of the oxidation dyeing of hair, oxidation dye precursors and couplers are sought which are capable, when they are combined, of creating shades which have satisfactory resistance to light, to washing, to inclement weather, to perspiration and to the various treatments to which the hair may be subjected.

Hitherto, these shades have been obtained with dyes based on para-phenylenediamine. However, it is currently sought to replace para-phenylenediamine. With this in mind, it has already been proposed to use para-phenylenediamines which are substituted on the benzene ring or on an amine function.

However, it appeared to the inventors that, in order to be even more satisfactory, the above dyes needed to be less selective, that is to say that they needed to be less sensitive, in dyeing terms, to the various degrees of sensitization of the hair to be dyed, so that the difference in colour observed on this more or less sensitized hair is as little as possible, and hence so that the hair is dyed uniformly.

Now, after considerable research conducted in this matter, the inventors have discovered that it is possible to obtain oxidation dyes based on para-phenylenediamine derivatives which are of markedly improved selectivity compared with those known hitherto, when a combination of at least two para-phenylenediamine derivatives is used, chosen from:

2-(β-hydroxyethyl)-para-phenylenediamine,
2-(β-hydroxyethyloxy)-para-phenylenediamine,
2,3-dimethyl-para-phenylenediamine,
2,6-dimethyl-para-phenylenediamine,
2,6-diethyl-para-phenylenediamine,
2-isopropyl-para-phenylenediamine,
N-(β-hydroxyethyl)-para-phenylenediamine,
N,N-di(β-hydroxyethyl)-para-phenylenediamine;

and the addition salts of these compounds with an acid, i.e., acid-addition salts.

This discovery forms the basis of the present invention.

The subject of the present invention is thus an oxidation dye composition for keratin fibers, in particular for human keratin fibers such as the hair, of the type comprising, in a medium which is suitable for dyeing, a combination of at least two oxidation dye precursors (oxidation bases) and, where appropriate, one or more couplers, wherein the para-phenylenediamine oxidation dye precursors are chosen from:

2-(β-hydroxyethyl)-para-phenylenediamine,
2-(β-hydroxyethyloxy)-para-phenylenediamine,
2,3-dimethyl-para-phenylenediamine,
2,6-dimethyl-para-phenylenediamine,
2,6-diethyl-para-phenylenediamine,
2-isopropyl-para-phenylenediamine,
N-(β-hydroxyethyl)-para-phenylenediamine,
N,N-di(β-hydroxyethyl)-para-phenylenediamine;

and the addition salts thereof with an acid, it being understood that the said combination cannot consist of:

a) the binary combination of N,N-di(β-hydroxyethyl)-para-phenylenediamine and N-(β-hydroxyethyl)-para-phenylenediamine; and b) the binary combination of 2-(β-hydroxyethyl)-para-phenylenediamine and 2,6-diethyl-para-phenylenediamine.

Preferably, said combination of at least two para-phenylenediamine oxidation dye precursors is not the ternary combination of 2-(β-hydroxyethyl)-para-phenylenediamine, 2,6-dimethyl-para-phenylenediamine and N-(β-hydroxyethyl)-para-phenylenediamine or the ternary combination of 2-(β-hydroxyethyl)-para-phenylenediamine, 2,6-dimethyl-para-phenylenediamine and 2-isopropyl-para-phenylenediamine.

Further preferably, the combination of para-phenylenediamine oxidation dye precursors does not include any combination of 2,3-dimethyl-para-phenylenediamine, 2,6-dimethyl-para-phenylenediamine, and 2,6-diethyl-para-phenylenediamine.

The novel dyes obtained within the context of the present invention make it possible to achieve less selective and thus more uniform coloration from the roots to the tips of the hair. They also have satisfactory resistance to external attack (light and rain), to perspiration and to various cosmetic hair treatments (permanent waving and shampooing).

Another subject of the present invention relates to a ready-to-use composition containing the various agents used to dye the keratin fibers defined above and an oxidizing agent.

The invention is also directed towards a process for dyeing keratin fibers, and in particular human keratin fibers such as the hair, which consists in applying to these fibers at least one composition (A) containing, in a medium which is suitable for dyeing, at least one combination of two oxidation dye precursors as has been defined above and, where appropriate, one or more couplers, the colour being developed at alkaline, neutral or acidic pH using an oxidizing agent which is mixed with composition (A) at the time of use or which is present in a composition (B) applied simultaneously or sequentially in a separate manner.

Another subject of the invention is multi-compartment dyeing devices or "kits", the first compartment of which contains at least one combination of at least two para-phenylenediamine derivatives listed above as oxidation dye precursors and, where appropriate, one or more couplers, and the second compartment of which contains an oxidizing agent.

However, other characteristics, aspects, subjects and advantages of the invention will emerge even more clearly on reading the description and the examples which follow.

The acid salts of the para-phenylenediamine derivatives which may be used according to the invention are preferably chosen from the hydrochlorides, the sulphates, the hydrobromides and the tartrates.

Among the combinations of at least two para-phenylenediamine derivatives, as oxidation dye precursors which may be used within the context of the present invention, it is preferred to use the following combinations:

2-(β-hydroxyethyl)-para-phenylenediamine and 2,6-dimethyl-para-phenylenediamine;

2-(β-hydroxyethyl)-para-phenylenediamine and N,N-di(β-hydroxyethyl)-para-phenylenediamine;

2-(β-hydroxyethyl)-para-phenylenediamine and N-(β-methoxyethyl)-para-phenylenediamine;

2,6-dimethyl-para-phenylenediamine and N,N-di(β-hydroxyethyl)-para-phenylenediamine;

2,6-dimethyl-para-phenylenediamine and N-(β-methoxyethyl)-para-phenylenediamine;

2,3-dimethyl-para-phenylenediamine and N,N-di(β-hydroxyethyl)-para-phenylenediamine;

2,3-dimethyl-para-phenylenediamine, N,N-di(β-hydroxyethyl)-para-phenylenediamine and 2,6-dimethyl-para-phenylenediamine;

2-(β-hydroxyethyl)-para-phenylenediamine, 2,6-dimethyl-para-phenylenediamine and 2,3-dimethyl-para-phenylenediamine;

2-(β-hydroxyethyl)-para-phenylenediamine, 2,6-dimethyl-para-phenylenediamine and N,N-di(β-hydroxyethyl)-para-phenylenediamine;

2,6-diethyl-para-phenylenediamine and 2,6-dimethyl-para-phenylenediamine;

2,6-diethyl-para-phenylenediamine and 2,3-dimethyl-para-phenylenediamine;

2,6-diethyl-para-phenylenediamine and N,N-di(β-hydroxyethyl)-para-phenylenediamine;

and the addition salts thereof with an acid.

The concentration of para-phenylenediamine derivatives or salts thereof in the combination may range from 0.01 to 10% by weight approximately relative to the total weight of the dye composition, and preferably approximately from 0.05 to 8% of this weight.

The oxidizing agent is preferably chosen from hydrogen peroxide, urea peroxide, alkali metal bromates, and persalts such as perborates and persulphates. It is particularly preferred to use hydrogen peroxide.

The composition (A), which includes the dye combination as described above, may have a pH approximately from 3 to 11, which may be adjusted to the chosen value either by using basifying agents commonly used in dyeing keratin fibers, such as aqueous ammonia, alkali metal carbonates, alkanolamines, for example mono-, di- and triethanolamine and derivatives thereof, sodium hydroxide or potassium hydroxide and the compounds of formula:

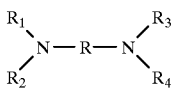

in which R is a propylene residue optionally substituted with a hydroxyl group or a $C_1$–$C_4$ alkyl radical; $R_1$, $R_2$, $R_3$ and $R_4$, simultaneously or independently of each other, represent a hydrogen atom, a $C_1$–$C_4$ alkyl radical or a $C_1$–$C_4$ hydroxyalkyl radical, or by using standard acidifying agents such as inorganic or organic acids like, for example, hydrochloric acid, tartaric acid, citric acid and phosphoric acid.

The pH of the composition (B) including the oxidizing agent as defined above is such that after mixing with the composition (A), the pH of the composition applied to the human keratin fibers preferably ranges approximately from 3 to 11. It is adjusted to the desired value using acidifying agents, or optionally basifying agents, which are well known to those skilled in the art, such as those described above.

The oxidizing composition (B) preferably consists of aqueous hydrogen peroxide solution.

According to a preferred embodiment of the dyeing process of the invention, the dye composition (A) described above is mixed, at the time of use, with an oxidizing solution in an amount which is sufficient to develop a coloration. The mixture obtained is then applied to the human keratin fibers and is left to stand for 2 to 40 minutes, preferably 5 to 30 minutes, after which the fibers are rinsed, washed with shampoo, rinsed again and dried.

As mentioned above, the preferred dye compositions according to the invention may also contain, besides the oxidation dye precursors defined above, one or more couplers. Among these couplers, there may more particularly be mentioned: 5-amino-2-methylphenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethyl)amino-1-methoxybenzene, sesamol, 6-hydroxyindole, 4-hydroxybenzimidazole, 6-hydroxy-1,4-benzoxazine, 4-amino-1,2-methylenedioxybenzene and 1-(β-hydroxyethyl)amino-3,4-methylenedioxybenzene. Other common couplers may be used.

In order to modify the shades or to enrich them with glints, the dye compositions may also contain, in addition to the oxidation dye precursors defined above and, where appropriate, combined couplers, additional oxidation dye precursors chosen from 2-aminophenol, 4-aminophenol, 4-amino-3-methylphenol, 4-amino-3-hydroxymethylphenol and 4-amino-3-fluorophenol, as well as direct dyes chosen from nitro dyes, azo dyes or anthraquinone dyes. Their concentration by weight may range approximately from 0.0005 to 10%, and preferably approximately from 0.001 to 5%, relative to the total weight of the dye composition applied to the hair.

The dye compositions may also contain antioxidants. These may be chosen in particular from sodium sulphite, thioglycolic acid, thiolactic acid, sodium bisulphite, dehydroascorbic acid, hydroquinone, 2-methylhydroquinone, tert-butylhydroquinone and homogentisic acid, and they are then generally present in proportions approximately from 0.05 to 1.5% by weight relative to the total weight of the composition.

In their preferred embodiment, the dye compositions according to the invention also contain surface-active agents that are well known to those skilled in the art, in proportions approximately from 0.5 to 55% by weight, and preferably from 2 to 50% by weight, relative to the total weight of the composition, organic solvents, in proportions approximately from 1 to 40% by weight, and in particular approximately from 5 to 30% by weight, relative to the total weight of the composition, or any other cosmetically acceptable adjuvant known in the prior art for the oxidation dyeing of hair.

Obviously, a person skilled in the art will take care when selecting this or these optional additional compounds so that the advantageous properties intrinsically associated with the combination in accordance with the invention are not, or are largely not, adversely affected by the addition or additions considered.

The composition applied to the hair may be in various forms, such as in liquid, cream or gel form or in any other form which is suitable for dyeing keratin fibers, and especially human hair. In particular, it may be packaged under pressure in an aerosol can in the presence of a propellant and may form a foam.

Concrete examples illustrating the invention will now be given.

In these examples, the selectivity criterion of the dye is evaluated by means of the colour variation index I calculated according to the following Nickerson equation (see in this regard "Journal of the Optical Society of America", 1944, September, Vol. 34, No. 9, pp. 550–570):

$$I = 0.4 C_0 \Delta H + 6 \Delta V + 3 \Delta C$$

in which the parameters H, V and C represent the parameters of the Munsell notation (ASTM standard D 1535-68) which defines the colour, H denoting the shade or HUE, V denoting the intensity or VALUE and C denoting the purity or CHROMATICITY; $C_0$ denotes the purity of the lock against which it is desired to evaluate the colour difference. The measurements are made on a MINOLTA CM 2002 colorimeter.

EXAMPLE

The following dye composition in accordance with the invention was prepared:

| | |
|---|---|
| 2-(β-Hydroxyethyl)-para-phenylene-diamine dihydrochloride | 0.5625 g |
| 2,6-Dimethyl-para-phenylenediamine dihydrochloride | 0.5225 g |
| Resorcine | 0.55 g |
| Oleyl alcohol polyglycerolated with 4 mol of glycerol, containing 78% active material (A.M.) | 5.7 g A.M. |
| Oleyl alcohol polyglycerolated with 2 mol of glycerol | 4.0 g |
| Oleic acid | 3.0 g |
| Oleylamine containing 2 mol of ethylene oxide, sold under the name Ethomeen O12 by the company Akzo | 7.0 g |
| Diethylaminopropyl laurylamino-succinamate sodium salt containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution containing 35% A.M. | 0.46 g A.M. |
| Ammonium acetate | 0.8 g |
| Antioxidant, sequestering agent | qs |
| Fragrance, preserving agent | qs |
| Aqueous ammuonia solution containing 20% NH$_3$ | 2.0 g A.M. |
| Demineralized water qs | 100.0 g |

In parallel, two comparative compositions (A) and (B) not forming part of the invention were prepared, which, in replacement for the combination of the two para-phenylenediamine derivatives: 2-(β-hydroxyethyl)-para-phenylenediamine and 2,6-dimethyl-para-phenylenediamine, contained:

Comparative Composition (A)

1.125 g of 2-(β-hydroxyethyl)-para-phenylenediamine dihydrochloride

Comparative Composition (B)

1.045 g of 2,6-dimethyl-para-phenylenediamine dihydrochloride

In these two comparative compositions, the concentration of para-phenylenediamine derivative was equal to the molar equivalent of the total concentration of the two para-phenylenediamine derivatives of the combination in accordance with the invention. The other constituents of the comparative compositions (A) and (B) were identical, in nature and in concentration, to those of the composition in accordance with the invention.

At the time of use, each of these three compositions, that of the invention, and the comparative compositions (A) and (B) not forming part of the invention, were mixed together weight for weight with 20-volumes aqueous hydrogen peroxide solution (6% by weight), of pH 3.

Three mixtures of pH 9.8 were obtained.

Each of these mixtures was applied for 30 minutes, to locks of non-permanent-waved grey hair containing 90% white hairs, on the one hand, and to locks of permanent-waved grey hair containing 90% white hairs, on the other hand. The hair was then rinsed, washed with shampoo, rinsed and dried.

The dyeing selectivity criteria associated with the compositions obtained were then assessed and compared.

Before dyeing, the non-permanent-waved grey hair containing 90% white hairs had a Munsell shade of: 4.2 Y 5.5/1.7.

Before dyeing, the permanent-waved grey hair containing 90% white hairs had a Munsell shade of: 4.0 Y 5.5/1.7.

The shades obtained after dyeing with each of the compositions are given in the table below:

| Composition | Colour on non-permament-waved hair | Colour on permanent-waved hair |
|---|---|---|
| Invention | 1.2 Y 4.6/2.2 | 1.5 Y 4.3/2.3 |
| A | 1.7 Y 4.4/2.2 | 1.7 Y 4.1/2.5 |
| B | 1.1 Y 4.4/2.3 | 1.1 Y 3.7/2.3 |

The differences in the rise of coloration, expressed by the Nickerson equation, between the permanent-waved hair and the non-permanent-waved hair (this rise being itself expressed, in each of these cases, by the difference in colour relative to an undyed lock), were as follows:

Composition in accordance with the invention: 1.76
Comparative composition (A): 2.56
Comparative composition (B): 4.06

These results demonstrated that a permanent-waved head of hair containing non-permanent-waved roots will have, after dyeing with the composition according to the invention containing the combination of two para-phenylenediamine derivatives, a more uniform coloration than with the dyeing operations performed with the comparative compositions (A) or (B) not forming part of the invention, since they each contained only one of the two para-phenylenediamine derivatives used in the composition of the invention.

What is claimed is:

1. An oxidation dye composition for keratin fibers comprising, in a medium which is suitable for dyeing, a combination of at least two para-phenylenediamine oxidation dye precursors and one or more couplers, wherein said combination is present in an amount effective to dye said keratin fibers, and said para-phenylenediamine oxidation dye precursors being:

2-(β-hydroxyethyl)-para-phenylenediamine,
2-(β-hydroxyethyloxy)-para-phenylenediamine,
2,3-dimethyl-para-phenylenediamine,
2,6-dimethyl-para-phenylenediamine, 2,6-diethyl-para-phenylenediamine, 2-isopropyl-para-phenylenediamine, N-(β-methoxyethyl)-para-phenylenediamine, N,N-di(β-hydroxyethyl)-para-phenylenediamine;

or an acid-addition salt of any of said para-phenylenediamine oxidation dye precursors, wherein said combination cannot consist of:

a) the binary combination of N,N-di(β-hydroxyethyl)-para-phenylenediamine and N-(β-hydroxyethyl)-para-phenylenediamine; or b) the binary combination of 2-(β-hydroxyethyl)-para-phenylenediamine and 2,6-diethyl-para-phenylenediamine.

2. The composition according to claim 1, wherein said combination of at least two para-phenylenediamine oxidation dye precursors is:

2-(β-hydroxyethyl)-para-phenylenediamine and 2,6-dimethyl-para-phenylenediamine;

2-(β-hydroxyethyl)-para-phenylenediamine and N,N-di(β-hydroxyethyl)-para-phenylenediamine;

2-(β-hydroxyethyl)-para-phenylenediamine and N-(β-methoxyethyl)-para-phenylenediamine;

2,6-dimethyl-para-phenylenediamine and N,N-di(β-hydroxyethyl)-para-phenylenediamine;

2,6-dimethyl-para-phenylenediamine and N-(β-methoxyethyl)-para-phenylenediamine;

2,3-dimethyl-para-phenylenediamine and N,N-di(β-hydroxyethyl)-para-phenylenediamine;

2,3-dimethyl-para-phenylenediamine, N,N-di(β-hydroxyethyl)-para-phenylenediamine and 2,6-dimethyl-para-phenylenediamine;

2-(β-hydroxyethyl)-para-phenylenediamine, 2,6-dimethyl-para-phenylenediamine and 2,3-dimethyl-para-phenylenediamine;

2-(β-hydroxyethyl)-para-phenylenediamine, 2,6-dimethyl-para-phenylenediamine and N,N-di(β-hydroxyethyl)-para-phenylenediamine;

2,6-diethyl-para-phenylenediamine and 2,6-dimethyl-para-phenylenediamine;

2,6-diethyl-para-phenylenediamine and 2,3-dimethyl-para-phenylenediamine;

2,6-diethyl-para-phenylenediamine and N,N-di(β-hydroxyethyl)-para-phenylenediamine;

or wherein in each of the above combinations, any or all of the para-phenylenediamines may be in the form of an acid-addition salt.

3. The composition according to claim 1, wherein said acid-addition salt of said para-phenylenediamine oxidation dye precursors is selected from the hydrochlorides, the sulphates, the hydrobromides or the tartrates.

4. The composition according to claim 1, wherein each of said para-phenylenediamine oxidation dye precursors or the acid-addition salts thereof in the combination is present in a concentration ranging from 0.01 to 10% by weight relative to the total weight of the composition.

5. The composition according to claim 4, wherein each of said para-phenylenediamine oxidation dye precursors or acid-addition salts thereof in the combination is present in a concentration ranging from 0.05 to 8% by weight relative to the total weight of the composition.

6. The composition according to claim 1, wherein said keratin fibers are human keratin fibers.

7. The composition according to claim 6, wherein said human keratin fibers are hair.

8. The composition according to claim 1, wherein said composition also contains at least one of a direct dye selected from nitro dyes, azo dyes or anthraquinone dyes or additional oxidation dye precursors selected from 2-aminophenol, 4-aminophenol, 4-amino-3-methylphenol, 4-amino-3-hydroxymethylphenol or 4-amino-3-fluorophenol.

9. The composition according to claim 1, wherein said composition is a ready-to-apply composition which contains an oxidizing agent and has a pH from 3 to 11.

10. A process for dyeing keratin fibers comprising the steps of:

applying to the fibers an amount of an oxidation dye composition as defined in claim 1, effective to develop color and developing colour in alkaline, neutral or acidic medium with the aid of an oxidizing agent which is added to said oxidation dye composition as defined in claim 1 at the time of said step of applying said oxidation dye composition to the fibers, or which oxidizing agent is present in a composition different from said oxidation dye composition, said different composition containing said oxidizing agent being applied simultaneously with or sequentially to said oxidation dye composition as defined in claim 1.

11. The process of claim 10, wherein said keratin fibers are human keratin fibers.

12. The process of claim 11, wherein said human keratin fibers are hair.

13. A multi-compartment device for dyeing keratin fibers comprising at least two compartments, one of which includes an oxidation dye composition as defined in claim 1, and another of which includes a composition different from said oxidation dye composition and comprising an oxidizing agent in a medium which is suitable for dyeing.

14. The device of claim 13, wherein said keratin fibers are human keratin fibers.

15. A process for dyeing keratin fibers comprising the step of applying to said fibers the contents of a multi-compartment dyeing device as defined in claim 13.

16. The process of claim 15, wherein said keratin fibers are human keratin fibers.

17. The process of claim 16, wherein said human keratin fibers are hair.

18. A process for the dyeing of keratin fibers to lower selectivity on said keratin fibers, said process comprising the step of dyeing said fibers in a medium suitable for dyeing with a combination of at least two para-phenylenediamine oxidation dye precursors and one or more couplers, wherein said combination is present in an amount effective to dye said keratin fibers, and said para-phenylenediamine oxidation dye precursors being:

2-(β-hydroxyethyl)-para-phenylenediamine, 2-(β-hydroxyethyloxy)-para-phenylenediamine, 2,3-dimethyl-para-phenylenediamine, 2,6-dimethyl-para-phenylenediamine, 2,6-diethyl-para-phenylenediamine, 2-isopropyl-para-phenylenediamine, N-(β-hydroxyethyl)-para-phenylenediamine, N,N-di(β-hydroxyethyl)-para-phenylenediamine;

or an acid-addition salt of any of said para-phenylenediamine oxidation dye precursors, to lower selectivity.

19. The composition according to claim 1, wherein said combination of at least two para-phenylenediamine oxidation dye precursors is:

2-(β-hydroxyethyl)-para-phenylenediamine and 2,6-dimethyl-para-phenylenediamine;

2-(β-hydroxyethyl)-para-phenylenediamine and N,N-di(β-hydroxyethyl)-para-phenylenediamine;

2-(β-hydroxyethyl)-para-phenylenediamine and N-(β-methoxyethyl)-para-phenylenediamine;

2,6-dimethyl-para-phenylenediamine and N,N-di(β-hydroxyethyl)-para-phenylenediamine;

2,6-dimethyl-para-phenylenediamine and N-(β-methoxyethyl)-para-phenylenediamine;

2,3-dimethyl-para-phenylenediamine and N,N-di(β-hydroxyethyl)-para-phenylenediamine;

2,3-dimethyl-para-phenylenediamine, N,N-di(β-hydroxyethyl)-para-phenylenediamine and 2,6-dimethyl-para-phenylenediamine;

2-(β-hydroxyethyl)-para-phenylenediamine, 2,6-dimethyl-para-phenylenediamine and 2,3-dimethyl-para-phenylenediamine;

2-(β-hydroxyethyl)-para-phenylenediamine, 2,6-dimethyl-para-phenylenediamine and N,N-di(β-hydroxyethyl)-para-phenylenediamine;

2,6-diethyl-para-phenylenediamine and N,N-di(β-hydroxyethyl)-para-phenylenediamine;

or wherein in each of the above combinations, any or all of the para-phenylenediamines may be in the form of an acid-addition salt.

\* \* \* \* \*